United States Patent [19]

Walker et al.

[11] Patent Number: 5,585,364
[45] Date of Patent: Dec. 17, 1996

[54] ANTIVIRAL COMPOUNDS

[75] Inventors: Richard T. Walker; Albert S. Jones, both of Birmingham, England

[73] Assignee: British Technology Group Limited, London, England

[21] Appl. No.: 467,903

[22] Filed: Jun. 6, 1995

Related U.S. Application Data

[63] Continuation of Ser. No. 271,250, Jul. 7, 1994, abandoned, which is a continuation of Ser. No. 603,666, Oct. 31, 1990, abandoned.

[30] Foreign Application Priority Data

Apr. 13, 1989 [GB] United Kingdom .................. 8908355

[51] Int. Cl.$^6$ ...................... A61K 31/505; A61K 31/52; A61K 31/70
[52] U.S. Cl. ................................ 514/47; 514/48; 514/51; 514/256; 514/261; 514/262; 514/263; 514/265; 514/266; 514/269; 536/26.7; 536/26.8; 536/27.14; 536/28.2; 549/30; 549/448; 549/472
[58] Field of Search ................................ 536/26.8, 28.2, 536/26.7, 27.14; 514/47, 48, 49, 50, 51, 256, 261–266, 269, 885; 549/30, 448, 472

[56] References Cited

U.S. PATENT DOCUMENTS

| | | | |
|---|---|---|---|
| 4,123,609 | 10/1978 | Behnke et al. | 536/27 |
| 4,837,311 | 6/1989 | Tam et al. | 536/27 |
| 5,026,688 | 6/1991 | Agrawal | 514/50 |

FOREIGN PATENT DOCUMENTS

| | | |
|---|---|---|
| 0284405 | 9/1988 | European Pat. Off. . |
| 0286425 | 10/1988 | European Pat. Off. . |
| 2009834 | 9/1970 | Germany . |

OTHER PUBLICATIONS

Sandström et al., Drugs, vol. 34, pp. 373–389, 1987.
Mitsuya et al., Retrovir in Human Lymph/Leukemia, Japan, Sci. Soc. Press / VNU Science Press, pp. 277–288, 1985.
Busso et al., Aids Research and Human Retroviruses, vol. 4, No. 6, pp. 449–455, 1988.

(List continued on next page.)

*Primary Examiner*—James O. Wilson
*Attorney, Agent, or Firm*—Nixon & Vanderhye

[57] ABSTRACT

Compounds of formula I or a pharmaceutically acceptable salt thereof:

$$R_1XArOP(OR_2)(OR_3),\quad\quad I$$

(with a C=O above the P)

in which formula $R_1$ represents an aliphatic hydrocarbyl group;

Ar represents a substituted or unsubstituted aromatic nucleus;

X represents $-SO_2-$ or $-CO-$ and $R_2$ and $R_3$ which may be identical or different represent moieties of formula (a), (b), (c), (d), (e), (f), (g), (h) or (i):

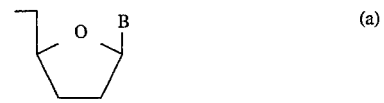

(a)

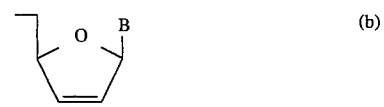

(b)

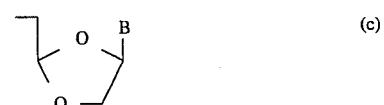

(c)

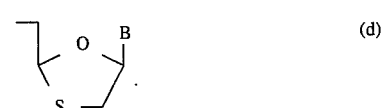

(d)

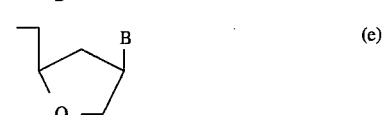

(e)

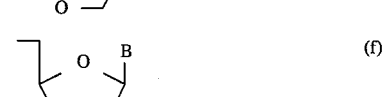

(f)

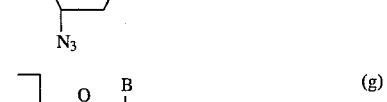

(g)

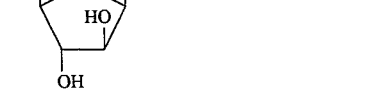

(h)

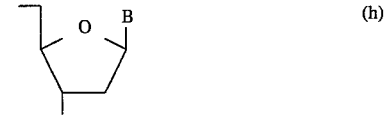

(i)

wherein B represents the residue of a nucleoside base of formula (A), (G), (C), (H) or (T):

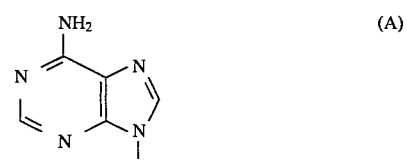

(A)

(Abstract continued on next page.)

-continued

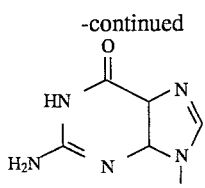 (G)

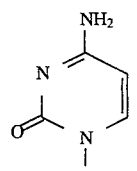 (C)

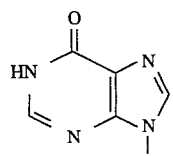 (H)

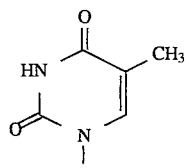 (T)

provided that when $R_2$ and $R_3$ both represent an unsubstituted moiety of formula (a) B represents the residue of a nucleoside base which is of formula (A), (G), (C) or (H) are of value for their antiviral activity.

23 Claims, No Drawings

OTHER PUBLICATIONS

March, Advanced Organic Chemistry, Reactions, Mechanisms, and Structure, McGraw–Hill, Inc., p. 1112, 1977.

Miyasaka et al, "A novel lead for specific anti–HIV–1 agents . . . ", Journal of Medicinal Chemistry, 1989, 32, 2507–2509.

Farrow et al, "Synthesis and Biological Properties of Novel Phosphotriesters . . . ", Journal of Medicinal Chemistry, 1990, 33, 1400–1406.

Reynolds (ed), "Zidovudine", Martindale –The Extra Pharmacopoeia, Twenty–ninth edition, The Pharmaceutical Press, London, 1989.

Extracts from Pharma Projects, PRB Publications Ltd., Richmond, England, 1989.

Chemical and Pharmaceutical Building, vol. 28, No. 10, Oct. 1980, M. Saneyoshi et al. pp. 2915–2923 see abstract; p. 2915, line 1 –p. 2916, end.

Chemische Berichte, vol. 108 No. 9, Sep. 1975, A. Myles et al, pp. 2857 –2871–see abstract; p. 2860 compounds 4, 14–19; p. 2861, lines 1–21; p. 2870, line 7 –p. 2871, end.

ANTIVIRAL COMPOUNDS

This is a Rule 62 continuation of application Ser. No. 08/271,250, filed 7 Jul. 1994, now abandoned, which is a Rule 62 continuation of application Ser. No. 07/603,666, filed 31 Oct. 1990, now abandoned.

This invention relates to antiviral compounds, the use thereof, processes for the production of such compounds and intermediates useful in such processes.

Whilst the antiviral compound azidothymidine (AZT) is used clinically to combat the Human Immunodeficiency Virus (HIV) it suffers from drawbacks, for example, toxicity to bone marrow cells. Compounds have now been found which offer the promise of reduction in such toxicity.

Accordingly, the present invention comprises a compound of formula I or a pharmaceutically acceptable salt thereof (e.g. a hydrochloride):

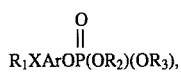

in which formula $R_1$ represents an aliphatic hydrocarbyl group e.g. an alkyl group which is preferably a $C_1$–$C_6$ alkyl group;

Ar represents a substituted or unsubstituted aromatic nucleus;

X represents —$SO_2$— or —CO— and $R_2$ and $R_3$ which, though usually identical may be different represent moieties of formula (a), (b), (c), (d), (e), (f), (g), (h) or (i):

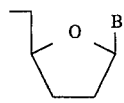 (a)

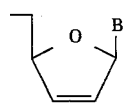 (b)

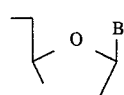 (c)

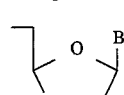 (d)

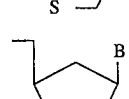 (e)

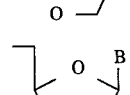 (f)

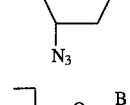 (g)

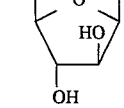 (h)

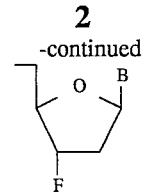

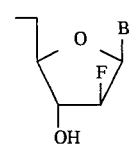 (i)

wherein B represents the residue of a nucleoside base of formula (A), (G), (C), (H) or (T):

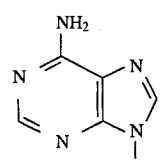 (A)

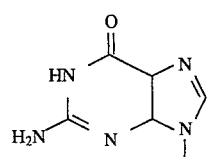 (G)

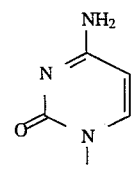 (C)

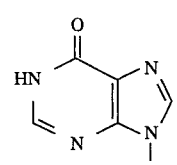 (H)

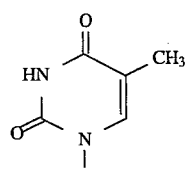 (T)

provided that when $R_2$ and $R_3$ both represent the moiety of formula (a) then B represents the residue of a nucleoside base which is of formula (A), (G), (C) or (H). It will be appreciated that (A), (G), (C), (H) and (T) represent the residues respectively of adenine, guanine, cytosine, hypoxanthine and thymine.

Typically, Ar represents a benzene ring in which the relative disposition of the group $R_1X$ and phosphate substituents is mutually para, the ring usually carrying no further substituents.

When, however, Ar represents a substituted aromatic nucleus, each substituent present is generally such that the compound hydrolyses readily to a corresponding phenol, $R_1XArOH$ which is not intolerably toxic.

Though Ar preferably represents an unsubstituted benzene ring, up to four substituents may be carried on the nucleus, those of particular interest including halogen e.g. chlorine, fluoroalkyl e.g. trifluoromethyl, alkoxy e.g. $C_1$–$C_4$ alkoxy, fluoroalkoxy, carboalkoxy e.g. $C_1$–$C_6$ carboalkoxy, amino, and amido. The alkyl group $R_1$ is generally unbranched and is typically a methyl group and X preferably represents a sulphonyl group.

Moieties $R_2$ and $R_3$ of special interest include: (i)–(x) and particularly (i), (v), (vi) and (ix).

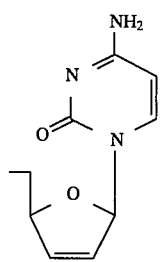 (i)

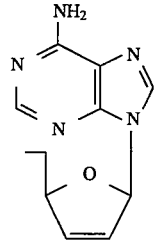 (ii)

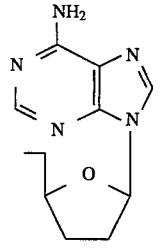 (iii)

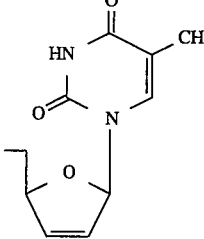 (iv)

(v)

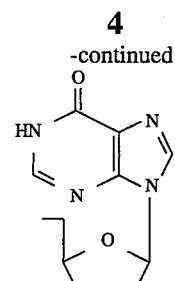 (vi)

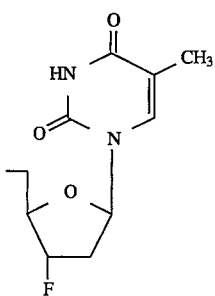 (vii)

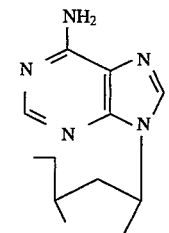 (viii)

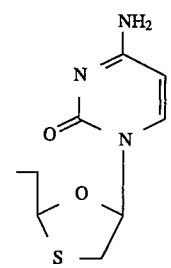 (ix)

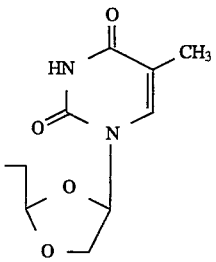 (x)

It will be appreciated that the moieties (i)–(vi) are found in compounds which may be represented by abbreviated nomenclature as (i) AZT, (ii) $d^4C$, (iii) $d^4A$, (iv) $d^2A$, (v) $d^4T$, (vi) ddI.

Compounds of the present invention may be produced in accordance with a further aspect thereof by reaction between a phosphorodihalidate of formula III: $R_1XArOP(O).Y_2$ (wherein Y represents halogen, e.g. chlorine) and a compound of formula $R_2OH$ (e.g. azidothymidine) or a derivative thereof e.g. a derivative in which a group in the nucleoside base is protected, as may be the free amino group in cytosine, by acetylation. The reaction is usually conducted in the presence of a base e.g. 1-methylimidazole and is typically conducted in an aprotic solvent such as acetonitrile.

Alternatively, when X represent $SO_2$, compounds of formula I may be produced in accordance with a further aspect of the present invention by oxidation of a compound of formula IV: $R_1SArOP(O)(OR_2)(OR_3)$ or of formula (V): $R_1SOArOP(O)(OR_2)(OR_3)$, oxidation typically being carried out with a per acid such as 3-chloroperbenzoic acid.

The present invention further includes within its scope intermediates of formula IV and formula V.

Compounds of the present invention find application in the treatment or prophylaxis of human retrovirus infections and particularly Human Immunodeficiency Virus (HIV) infection which gives rise to Acquired Immune Deficiency Syndrome (AIDS).

Accordingly, in a further aspect the invention comprises a compound of formula I for use in therapy and in a yet further aspect of the present invention the use of a compound of formula I for the manufacture of a medicament useful in the treatment or prophylaxis of a human retrovirus infection, particularly HIV, or of Acquired Immuno Deficiency Syndrome.

The dosage form and amount can be readily established by reference to known treatment or prophylactic regimens. In general however the dosage of the compound of formula I will be lower than the corresponding amount of AZT and usually lies within the range about 50 to about 800 mg.

While it is possible for the active compound of formula I or pharmaceutically acceptable salt thereof to be administered alone, it is preferable to present the active compound as a pharmaceutical formulation. Formulations of the present invention, for medical use, comprise the active compound together with one or more pharmaceutically acceptable carriers thereof and, optionally, any other ingredients which may be therapeutical per se, synergistic with the compound of formula I, or both. Carrier(s) must be pharmaceutically acceptable in the sense of being compatible with the other ingredients of the formulation and not deleterious to the recipient thereof.

The present invention therefore further provides a pharmaceutical formulation comprising a compound of formula (I) (in the form of the free base or a pharmaceutically acceptable acid addition salt) together with a pharmaceutically acceptable carrier thereof.

The formulations include those suitable for oral, rectal, topical or parenteral (including subcutaneous, intramuscular and intravenous) administration.

The formulations may conveniently be presented in unit dosage form and may be prepared by any of the methods well known in the art of pharmacy. All methods include generally the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol for example glycerol or sorbitol.

Formulations for rectal administration may be presented as a suppository with a usual carrier such as cocoa butter.

Formulations suitable for parental administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

The present invention is illustrated by the following Example:

EXAMPLE 1

Preparation of 4-(methylsulphonyl)phenyl bis (3'-azido thymidin-5'-yl) phosphate A. 4-(Methylsulphonyl)phenyl phosphorodichloridate 4-(Methylthio)phenyl phosphorodichloridate. To a solution of freshly distilled phosphoryl chloride (45 ml, 0.5 mol) and 1-methylimidazole (0.15 ml), is added 4-(methylthio)phenol (14, 0.1 mol) and the solution is heated under reflux for 20 h. The excess of phosphoryl chloride is removed by distillation and the residue distilled under reduced pressure to give the product (11 g, 42% yield); bp 135°–142° C. (2 mm Hg) $^1$H NMR (CDCl$_3$) δ 2.39 (3H, S, SCH$_3$), 7.22 (4 H, s, phenyl).

4-(methylsulphonyl)phenol. To a solution of 4-(methylthio)phenol (7.0 g. 0.05 mol) in 30% aqueous methanol (100 ml) at 0° C. is added a solution of sodium periodate (10.7 g, 0.05 mmol) and the resulting suspension is stirred for 30 min. Water (500 ml) is then added and the precipitate removed by filtration. The filtrate is cooled to 4° C. and a further portion of sodium periodate (10.7 g, 0.05 mmol) added and the resulting suspension stirred for 48 h when a further portion of sodium periodate (5.35 g, 0.025 mmol) is added. After stirring for a further 18 h, the precipitate is removed by filtration, the filtrate extracted with ether which is evaporated to dryness and the residue is purified on a silica column using chloroform methanol, 9:1, as eluent to give the title compound (2.75 g, 32% yield).

4-(Methylsulphonyl)phenol phosphorodichloridate. 4-(Methylthio)phenol (3.0 g, 17 mmol) is heated under reflux with freshly distilled phosphoryl chloride (13.35 ml, 87 mmol) and 1-methylimidazole (0.05 ml) for 20 h. The excess of phosphoryl chloride is removed by distillation and the residue is distilled under reduced pressure to give the title compound (bp 185° C. 1 mm Hg) as a yellow oil which solidifies on cooling (500 mg, 10% yield).

B. 4-(methylsulphonyl)phenyl bis (3'-azidothymidin-5'-yl)phosphate

4(methylsulphonyl)phenyl phosphorodichloridate (52 mg 0.018 mmol), 1-methylimidazole (0.08 ml 0.92 mmol) and dry acetonitrile (3 ml.) are stirred for 5 minutes at room temperature under dry nitrogen. The addition of Azido thymidine (80 mg 0.3 mmol) in 1 ml of dry acetonitrile follows. The resulting suspension is then stirred overnight at room temperature. Thin Layer Chromatography (Tlc) of the reaction mixture shows only ca. 25% of the slower moving spot in $CHCl_3$:MeoH (9:1). At this stage another equivalent of 4-(methylsulphonyl)phenyl phosphorodichloridate and 1-methylimidazole in dry acetonitrile is added and the reaction mixture is stirred for a further 48 hours. Tlc then shows ca. 90% conversion to the slower moving component. After addition of phosphate buffer (15 ml. pH 6.0) the mixture is extracted with chloroform (4×10 ml). The chloroform extracts are washed with water and then dried over magnesium sulphate. The chloroform is evaporated under reduced pressure and the residue is applied, pre-absorbed onto silica gel. to a short silica gel column (80 g, type 7734). The column is eluted with chloroform:methanol (9:1). The appropriate fractions are concentrated to give a white solid (115 mg., 52%).

NMR Spectrum ($^1H$)$\delta$($d_6$DMSO): 11.36(2H,S,NH), 7.95(2H,d,phenyl) 7.5S(2H,d,H-6), 7.45(2H,d,phenyl), 6.14(2H,t,—H-$1^1$), 4.4S(2H,m,H-$3^1$), 4.04(2H,m,H-$4^1$), 3.42(4H,m,H-$S^1$), 3.21(3H,S,$SO_2CH_3$) 2.44(4H,m,H-$2^1$), 1.71(6H,S, $CH_3$)

Elemental Analysis:

Found: C, 42.9; H, 4.5; N, 18.9; $C_{27}H_{31}N_{10}O_{12}P5$ requires C, 43.2; H, 4.16; N, 18.66%.

Mass Spectrum

M/Z 751 $(M+H)^+$. 773 $(M+Na)^+$.

EXAMPLE 2

Preparation of 4-(Methylsulphonyl)phenyl bis (3-azido thymidin-5'-yl)phosphate via 4-(methylthio)phenyl analogue 4-Methylthio)phenyl bis (3'-azidothymidin-5'-yl) phosphate (144 mg, 0.2 mmol), prepared by reaction of 4-(methylthio)phenyl phosphorodichloridate (Example 1A) with azido thymidine) is dissolved in dry ethanol and cooled to 0° C. A solution of 3-chlorperoxybenzoic acid (107 mg, 0.6 mmol) in dry ethanol (15 ml) is added dropwise with stirring over 15 minutes. The resulting solution is stored overnight at 5° C. After this period, Tlc (chloroform-methanol (9:1)) shows ca. 90% conversion to a slower-moving component. The solvent is evaporated under reduced pressure and the residue is applied, pre-absorbed onto silica gel, to a silica gel column (10 g, type 9385). The column is eluted with chloroform-methanol (9:1). The appropriate fractions are concentrated and purified further using the chromatotron (2 mm plate, same solvent system). The product is isolated as a white solid (105 mg. 70%).

A sample of the compound 4-(methylsulphonyl)phenyl bis 3'-azidothymidin-5'-yl phosphate is shown by HPLC analysis in reverse phase chromatography to consist of 4 components: azidothymidine (AZT) as a minor component, 4-(methylsulphonyl) phenyl bis 3' azidothymidin-5'-yl phosphate, the latter compound without the side chain on the ester linkage and an unidentified component.

The sample, considered of adequate quality for antiviral testing is assayed as follows:

Anti-HIV Testing

The assays are carried out in 96 well (microtitre) panels using the MT4 cell line, infe3cted with IOTCID50 of HIV 3B. The antiviral activity and cytotoxicity of each compound is assayed simultaneously. Three compounds are screened on each panel. Each compound is tested at 100.0, 10.0, 1.0 and 0.1 µM, unless otherwise stated. AZT is included in each assay as a positive control at 10.0, 1.0, 0.1 and 0.01 µM.

The antiviral activity (in infected cells) and cytotoxicity (to uninfected cells) of each compound is determined by measuring the number of viable cells remaining after 5 days incubation of 37° C. and comparing them with infected or uninfected controls. The number of viable cells is determined by the addition of the tetrazolium dye MTT. MTT uptake and conversion to a blue Formazan derivative has been shown to be linear with viable cell number. Following MTT addition, the cells are solubilised with acidified isopropanol and the extent of MTT conversion is measured spectrophotometrically.

Antiviral activity is apparent through the ability of compounds to protect the cells from virus induced cytopathic effect. The result is reported as the percentage of cells protected at a given drug concentration.

The results of the assay are shown in the Table

TABLE

| Concentration of BTG 17041: | % Protection | | | | | | |
|---|---|---|---|---|---|---|---|
| | 100 | 10 | 1.0 | 0.1 | 0.01 | 0.001 µM | MTC |
| Antiviral Activity: | 13% | 79% | 91% | 91% | 21% | 9% | 100 µM |

It can be seen from the Table that concentrations of BTG 1704 between 0.1 and 10 µM offers significant protection of MT4 cells from HIV-1 cytopathic effect. The toxic concentration of the drug is estimated to be about 100 µM. This is not however a quantitative test for cytotoxicity.

EXAMPLE 3

4-(Methylsulphonyl)phenyl bis (2',3'-didehydro-2',3'-dideoxy cytidin-5'-yl)phosphate $N^4$-acetyl-2',3'-didehydro-2',3'-deoxycytidine: 2',3'-didehydro-2',3'-dideoxycytidine (36.2 mmol) is suspended into dry methanol (100000 ml) and heated to reflux. Dry acetic anhydride (10 ml, 106 mmol) is added 4 times at every hour (total amount 40 ml,. 0.42 mol). The reaction mixture is finally stirred for 6 hr. at refluxed temperature and then left overnight at room temperature. The precipitated crystal is filtered out and washed with ethanol. (73% yield).

4-(Methylthio)phenyl bis ($N^4$-acetyl-2',3'-didehydro-2',3'-dideoxycytidin-5'-yl)phosphate 4-(methylthio)phenyl phosphorodichloridate, dry 1-methyl-imidazole and dry acetonitrile are stirred vigorously for 5 min. and then added to a solution of $N^4$-acetyl-2',3'- didehydro'2',3'-dideoxycytidine in acetonitrile. After stirring for several hours at room temperature, phosphate buffer is added (pH 6.0) and the mixture is extracted with chloroform. The chloroform extracts are washed with water and then dried over magnesium sulphate. The chloroform is evaporated under reduced pressure and the residue is applied, pre-absorbed, onto silica gel, to a short silica gel column. The column is eluted and the resulting material is further purified using a chromatotron (2 mm plate). The product is then isolated.

4-(Methylthio)phenyl bis (2',3'-didehydro-2',3'-dideoxy-cytidin-5'-yl)phosphate 4-(Methylthio)phenyl bis (2',3'-didehydro-2',3'-dideoxycytidin-5'-yl)phosphate 4-(Methylthio)phenyl bis($N^4$-acetyl-2'3,'-didehydro-2',3'-dideoxycytidin-5'-yl)phosphate 4-(methylthio)phenyl bis($N^4$-acetyl-2',3'-didehydro-2',3'-dideoxycytidin-5'-yl)phosphate is stirred with potassium carbonate/methanol solution for 20 hrs. at room temperature. After this period the solvent is evaporated under reduced pressure and the residue is applied, pre-absorbed, onto silica gel, to a short silica gel column. The column is eluted and the product is isolated.

4-(Methylsulphonyl)phenyl bis(2',3'-didehydro-2',3'-dideoxycytidin-5'-yl)phosphate 4-(Methylthio)phenyl bis(2',3'-didehydro-2',3'-dideoxycytidin-5'-yl)phosphate is dissolved in dry ethanol and cooled to 0° C. A solution of 3-chloroperoxybenzoic acid is added dropwise with stirring over 10 min. and the mixture is stored for 15 hrs. at 5° C. After this period, TLC shows complete conversion of starting material to a major component together with a minor impurity. The solvent is removed by evaporation under reduced pressure and the residue is applied to a 2 mm chromatotron plate in a small volume of chloroform, and then eluted. This purification step is repeated and the product is isolated.

EXAMPLE 4

4-(Methylsulphonyl)phenyl bis(2',3'-didehydro-2',3'-dideoxyadenosin-5'-yl)phosphate 4-(Methylsulphonyl)phenyl phosphorodichloridate (86 mg, 0.3 mmol), dry 1-methylimidazole (0.13 ml, 1.4 mmol) and dry pyridine (20 ml) are stirred for 5 min. and then added to 2',3'-didehydro-2',3'-dideoxyadenosine (100 mg, 0.4 mmol). The reaction mixture is stirred vigorously for 18 hrs. at room temperature. T.l.c. shows ca. 50% conversion of starting material to a slower-moving component. A further portion of "phosphorylating agent" (86 mg, 0.3 mmol and 0.13 ml, 1.4 mmol 1-methylimidazole) is added and the reaction is again stirred for 24 hours. After this period, t,l,c shows still ca. 50% conversion to the slower-moving component. The reaction mixture is evaporated to dryness under reduced pressure. The residue is applied, pre-absorbed onto silica gel, to a silica gel column and eluted with chloroform:methanol (10:1). The required fractions are collected and evaporated to dryness, and then dissolved in a minimum of chloroform and triturated with addition of hexane to give the product (23 mg, 16% yield).

NMR Spectrum: $\delta(d_6DMSO)$ 3.19(3H, s, $SO_2CH_3$), 4.24 (2H, s, 2×H-5'), 5.04 (2H, s, 2× H-4'), 6.26 (2H, t, 2x H-1'), 6.42 (2H, s, 2×H-3', 6.96 (2H, s, 2×H-2'), 7.32 (4H, d, 2×$NH_2$), 7.22–7.77 (4H, dd, phenyl), 8.07 (2H, d, 2×h-2), 8.16 (2H, s, 2×H-8)

FAB Mass Spectrum: m/z 683 [M+H]$^+$

EXAMPLE 5

4-(Methylsulphonyl)phenyl bis(2',3'-dideoxyadenosin-5'-yl) phosphate 4-(Methylsulphonyl)phenyl phosphorodichloridate (87 mg, 0.3 mmol), dry 1-methylimidazole (0.13 ml, 1.4 mmol) and dry pyridine (20 ml) are stirred for 5 min. and then added to 2',3'-dideoxyadenosine (120 mg, 0.5 mmol). The reaction mixture is stirred for 16 hours at room temperature under a stream of nitrogen. T.l.c. shows ca. 40% conversion of starting material to a slower-moving component. A further portion of "phosphorylating agent" (87 mg, 0.3 mmol and 0.13 ml, 0.3 mmol 1-methylimidazole) is added and the reaction mixture is again stirred for 24 hours. The reaction mixture is evaporated to dryness under reduced pressure. The residue is applied, pre-absorbed onto silica gel, to a slica gel column and chromatograph, eluting with dichloromethane:methanol (20:3).

NMR Spectrum: $\tilde{\delta}(d_6DMSO)$ 2.08 (4H, m, 2×H-2'), 2.80 (4H, m, 2×H-3'), 3.92 (4H, m, 2×H-5'), 4.26 (2H, s, 2×H-4'), 6.24 (2H, m, 2×H-1'), 7.26 (4H, s, 2×$NH_2$), 7.31–7.84 (4H, m, phenyl), 8.13 (2H, s, 2×H-2), 8.27 (2H, s, 2×H-8).

FAB Mass Spectrum: m/z 687 [M+H]$^+$

EXAMPLE 6

4-(Methylsulphonyl)phenyl bis(2',3'-didehydro-2',3'-dideoxythymidin-5'-yl)phosphate 4-(Methylsulphonyl)phenyl phosphodichloridate (58 mg, 0.2 mmol), dry 1-methylimidazole (85 μl, 1.0 mmol) and dry acetonitrile (5 ml) are stirred vigorously for 5 min. and then added to a solution of 2',3'-didehydro-2',3'-dideoxythymidine (70 mg, 0.3 mmol) in dry acetonitrile (5 ml). After stirring for 17 hours at room temperature under a stream of nitrogen, t.l.c. (chloroform:methanol=10:1) shows ca. 60% conversion to a slower-moving component. A further portion of "phosphorylating agent" (22 mg, 0.1 mmol and 0.4 ml, 0.4 mmol 1-methylimidazole) is added, and after stirring for 26 hrs., a further portion of "phosphorylating agent" (13 mg, 0.05 mmol and 0.4 ml, 0.4 mmol 1-methylimidazole) is added. The reaction mixture is stirred at 37° C. for 18 hours, but t.l.c. shows the conversion of 60% is not improved at all. After addition of phosphate buffer (20 ml, pH 6.0), the mixture is extracted with chloroform. The organic layer is dried (magnesium sulphate), then evaporated to dryness under reduced pressure. The residue is purified by silica gel column chromatography with ether:methanol (5:1) as eluent to give the product (35 mg, 34% yield).

NMR Spectrum: $\delta(d_6DMSO)$ 1.65 (6H, d, 2×$CH_3$), 3.25 (3H, s $SO_2CH_3$), 4.35 (4H, m, 2×H-5'), 4.95 (2H, s, 2×H-4'), 6.05 (2H, m, 2×H-3'), 6.40 (2H, m, 2×H-2'), 6.85 (2H, s, 2×H-1'), 7.25–7.40 (4H, dd, phenyl), 7.90 (2H, m, 2×H-6), 11.35 (2H, d, 2×NH).

FAB Mass Spectrum: m/z 665 [M+H]$^+$

Elemental Analysis: Found: C, 48.9; H, 4.6; N, 8.5. $C_{27}H_{29}O_{12}N_4PS$ requires C, 48.8; H, 4.4; N, 8.4%.

We claim:

1. A compound of formula (I) or a pharmaceutically acceptable salt thereof:

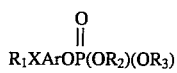 (I)

in which $R_1$ represents a $C_{1-6}$ alkyl group; Ar represents a phenylene group which is unsubstituted or substituted by 1 to 4 members selected from the group consisting of halogen, $C_{1-6}$ fluoroalkyl, $C_{1-4}$ alkoxy, $C_{1-4}$ fluoroalkoxy, $C_{1-6}$ carboalkoxy, amino or amido, x represents —$SO_2$— or —CO— and $R_2$ and $R_3$ are selected from the group consisting of formulae (a), (b), (c), (d), (e), (f), (g), (h) or (i):

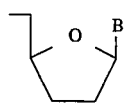 (a)

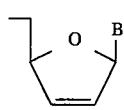 (b)

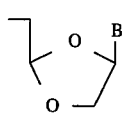 (c)

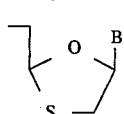 (d)

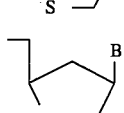 (e)

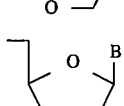 (f)

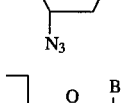 (g)

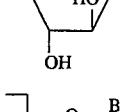 (h)

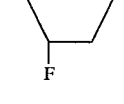 (i)

wherein B represents a nucleoside base moiety selected from the group consisting of formulae (A), (G), (C), (H) or (T):

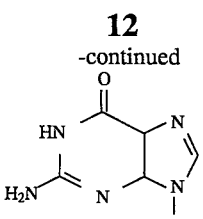 (A)

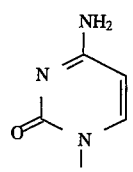 (G)

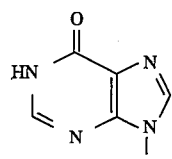 (C)

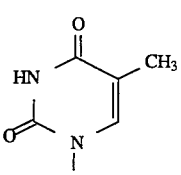 (H)

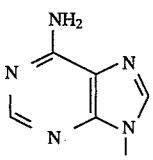 (T)

with the proviso that when $R_2$ and $R_3$ both represent the moiety of formula (a), then B is a member selected from the group consisting of (A), (G), (C) or (H).

2. A compound of claim 1, in which Ar is an unsubstituted phenylene group.

3. A compound of claim 1, in which the group $R_1X$ is para to the group $OP(O)(OR_2)(OR_3)$.

4. A compound of claim 1, in which $R_1$ is a methyl group.

5. A compound of claim 1, in which X is a sulphonyl group.

6. A compound of claim 1, in which $R_1XAr$ is a 4-(methylsulphonyl)phenyl group.

7. A compound of claim 1 in which $R_2$ and $R_3$ are independently selected from the group consisting of (a), (b), (d) or (f).

8. A compound of claim 1, in which $R_2$ and $R_3$ are formula (f).

9. A compound of claim 1, in which $R_2$ and $R_3$ are selected from the group consisting of the formulae (i), (ii), (iii), (iv), (v), (vi), (vii), (viii), (ix) or (x):

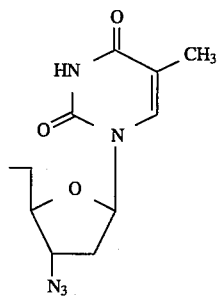 (i)

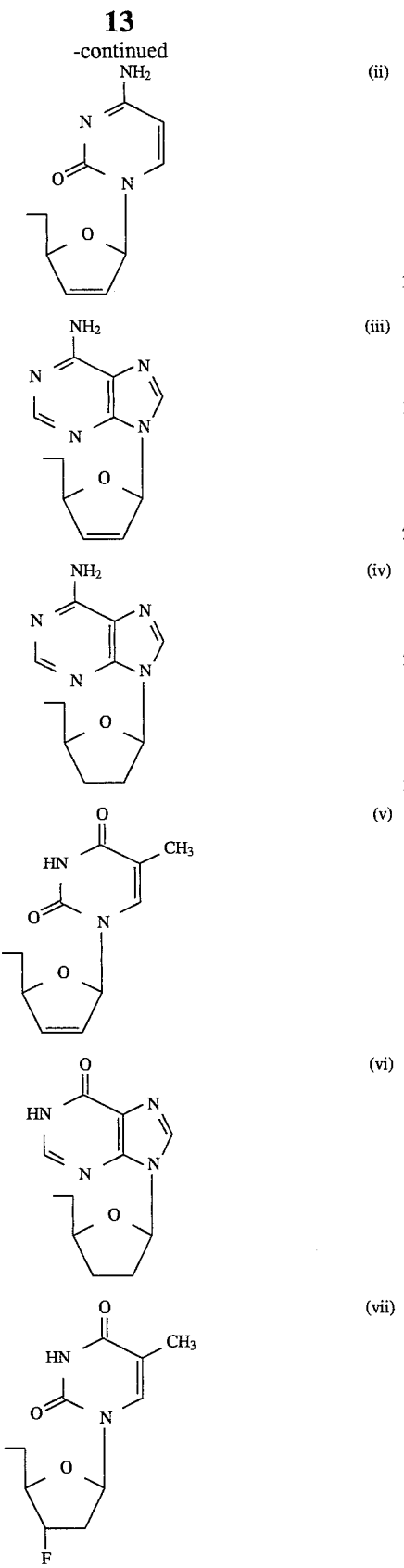

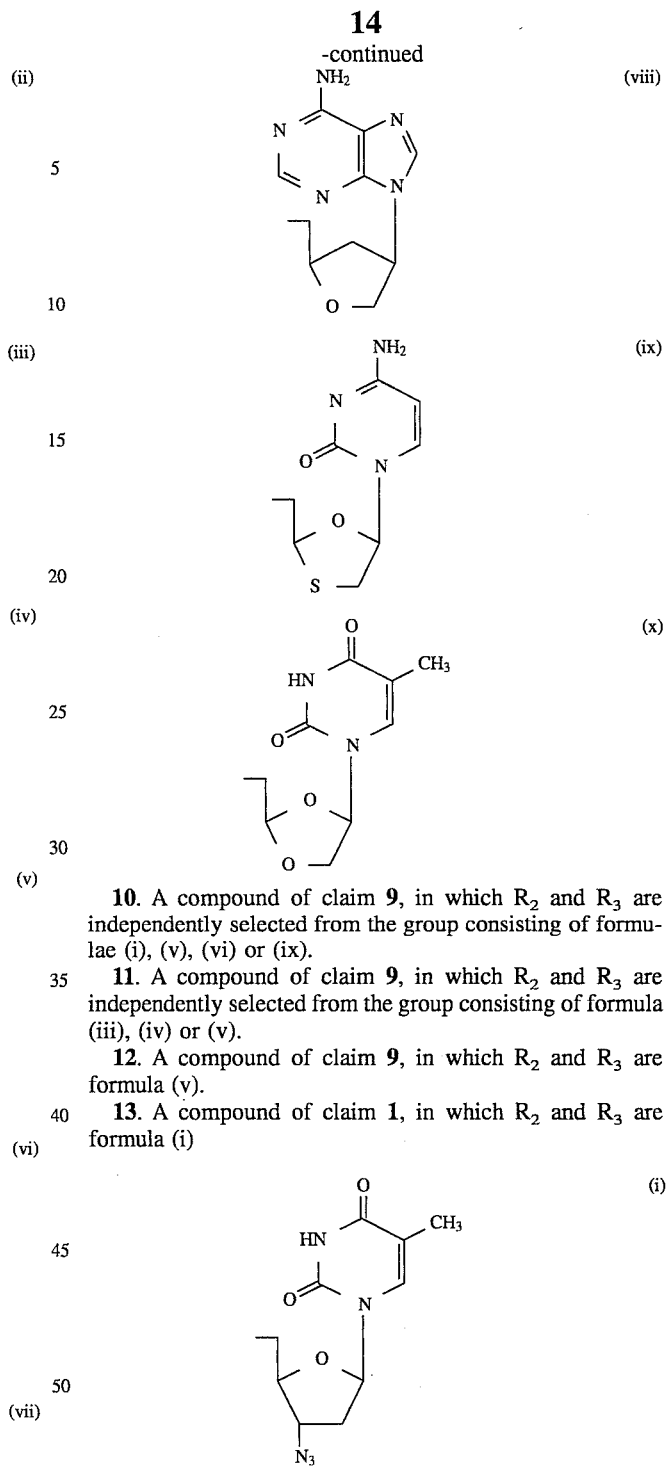

10. A compound of claim 9, in which $R_2$ and $R_3$ are independently selected from the group consisting of formulae (i), (v), (vi) or (ix).

11. A compound of claim 9, in which $R_2$ and $R_3$ are independently selected from the group consisting of formula (iii), (iv) or (v).

12. A compound of claim 9, in which $R_2$ and $R_3$ are formula (v).

13. A compound of claim 1, in which $R_2$ and $R_3$ are formula (i)

14. A compound of formula (I) or a pharmaceutically acceptable salt thereof:

in which $R_1$ is a $C_{1-6}$ group, Ar is a phenylene group which is unsubstituted or substituted 1 to 4 members selected from the group consisting of halogen, $C_{1-4}$ alkoxy, $C_{1-6}$ carboalkoxy, amino or amido, X represents —$SO_2$— and $R_2$ and $R_3$ are formula (i):

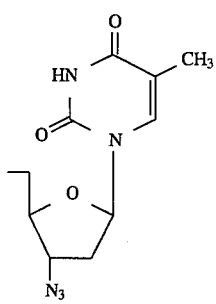

(i)

15. 4-(Methylsulphonyl)phenyl bis(3'-azido thymidin-5'-yl)-phosphate.

16. 4-(Methylsulphonyl)phenyl bis(2',3'-didehydro-2',3'-dideoxy cytidin-5'-yl)phosphate.

17. 4-(Methylsulphonyl)phenyl bis(2',3'-didehydro-2',3'-dideoxy adenosin-5'-yl)phosphate.

18. 4-(Methylsulphonyl)phenyl bis(2',3'-dideoxy adenosin-5'-yl)phosphate.

19. 4-(Methylsulphonyl)phenyl bis(2',3'-didehydro-2',3'-dideoxy-thymidin-5'-yl)phosphate.

20. A compound of formula (IV), represented by the formula $R_1SArOP(O)(OR_2)(OR_3)$, in which formula $R_1$, Ar, $R_2$ and $R_3$ are as defined in claim 1.

21. A compound of formula (V), represented by the formula $R_1SOArOP(O)(OR_2)(OR_3)$, in which formula $R_1$, Ar, $R_2$ and $R_3$ are as defined in claim 1.

22. A pharmaceutical formulation which comprises an effective amount of a compound of formula (I) as defined in claim 1 together with a pharmaceutically acceptable carrier therefor.

23. A formulation according to claim 22, in dosage form.

* * * * *